United States Patent
Pulford et al.

(10) Patent No.: US 6,723,044 B2
(45) Date of Patent: Apr. 20, 2004

(54) ABDOMINAL RETRACTOR

(75) Inventors: John C. Pulford, Groton, MA (US); Marco Pelosi, New Providence, NJ (US)

(73) Assignee: Apple Medical Corporation, Marlboro, MA (US)

( * ) Notice: Subject to any disclaimer, the term of this patent is extended or adjusted under 35 U.S.C. 154(b) by 187 days.

(21) Appl. No.: 10/097,421

(22) Filed: Mar. 14, 2002

(65) Prior Publication Data

US 2003/0176771 A1 Sep. 18, 2003

(51) Int. Cl.⁷ .......................... A61B 17/02; A61B 19/00
(52) U.S. Cl. ................... 600/208; 600/206; 128/850; 128/856
(58) Field of Search ................ 600/206, 207, 600/208, 209, 210, 201, 203; 128/849, 850, 851, 852, 853, 854, 855, 856

(56) References Cited

U.S. PATENT DOCUMENTS

| | | |
|---|---|---|
| 1,196,250 A | 8/1916 | Kuhn |
| 1,810,466 A | 6/1931 | Deutsch |
| 2,305,289 A | 12/1942 | Coburg |
| 2,739,587 A | 3/1956 | Scholl |
| 3,111,943 A | 11/1963 | Orndorff |
| 3,332,417 A | 7/1967 | Blanford et al. |
| 3,347,226 A | 10/1967 | Harrower |
| 3,347,227 A | 10/1967 | Harrower |
| 3,397,692 A | 8/1968 | Creager, Jr. et al. |
| 3,416,520 A | 12/1968 | Creager, Jr. |
| 3,476,109 A | 11/1969 | Hurney |
| 3,523,534 A | 8/1970 | Nolan |
| 3,841,332 A | 10/1974 | Treacle |
| 4,043,328 A | 8/1977 | Cawood, Jr. et al. |
| 4,188,945 A | 2/1980 | Wenander |
| 4,553,537 A | 11/1985 | Rosenberg |
| 4,926,851 A | 5/1990 | Bulley |
| 5,159,921 A | 11/1992 | Hoover |
| 5,178,133 A | 1/1993 | Pena |
| 5,263,922 A | 11/1993 | Sova et al. |
| 5,366,478 A | 11/1994 | Brinkerhoff et al. |
| 5,480,410 A | 1/1996 | Cuschieri et al. |
| 5,514,123 A | 5/1996 | Adolf et al. |
| 5,522,791 A | 6/1996 | Leyva |
| 5,524,644 A | 6/1996 | Crook |
| 5,636,645 A | 6/1997 | Ou |
| 5,640,977 A | 6/1997 | Leahy et al. |
| 5,649,550 A | 7/1997 | Crook |
| 5,803,921 A | 9/1998 | Bonadio |
| 5,853,395 A | 12/1998 | Crook |
| 5,906,577 A | 5/1999 | Beane et al. |
| 6,382,211 B1 | 5/2002 | Crook |

FOREIGN PATENT DOCUMENTS

| | | |
|---|---|---|
| AU | 165664 | 3/1954 |
| FR | 484 539 A | 10/1917 |
| GB | 858821 | 1/1961 |
| WO | WO 99/03416 | 1/1999 |

OTHER PUBLICATIONS

US 4,777,493, 10/1988, Chvapil (withdrawn)

*Primary Examiner*—Kevin Shaver
*Assistant Examiner*—David Comstock
(74) *Attorney, Agent, or Firm*—Kudirka & Jobse, LLP

(57) ABSTRACT

An adjustable retractor is disclosed comprising an inner ring, an outer ring spaced from the inner ring, and an elongate sleeve open at opposite ends. The sleeve is provided and extends between the inner and outer rings and is connected at the opposite ends to the rings. The outer ring is provided with a pre-loaded rotational torque to assist with rotation of the outer ring about its central axis to roll the sleeve about the outer ring to adjust sleeve length. The outer ring may be formed in a mobius configuration to provide the pre-loaded rotational torque. The outer ring has a cross-sectional shape that may have numerous different configurations. The mobius configuration may include the cross-sectional shape having an outer circumference offset by a predetermined amount about the central axis of the outer ring proceeding longitudinally along the central axis from one location on the outer ring to another location on the outer ring. A method of adjusting a retractor is also disclosed.

42 Claims, 2 Drawing Sheets

ABDOMINAL RETRACTOR

FIELD OF THE INVENTION

The present invention relates generally to surgical retractors, and more particularly to adjustable surgical retractors for use in expanding incisions performed during surgery.

BACKGROUND OF THE INVENTION

Abdominal retractors are well known, and are typically used during surgery to expand incisions so that body parts under the incision may be accessed by the surgeon. One well-known type of abdominal retractor is a metal retractor. Metal retractors are typically placed at opposite sides of the incision to expand the incision for surgery. Metal retractors have often been used with cotton sponges held against the sides of the incision by the retractors.

Other types of retractors include wound edge protectors. Examples of wound edge protectors include those shown in U.S. Pat. Nos. 3,347,226 and 3,347,227. However, these wound edge protectors do not adjust the vertical length of the sleeve. Wound edge protectors typically have an inner ring spaced from an outer ring with a flexible sheet of material formed into a sleeve extending between the rings and connected at opposite ends to the rings. During surgery, the inner ring is squeezed into an oblong shape to be inserted through the wound and to be allowed to expand against the inside edge of the wound. The outer ring overlaps the outside edge of the wound to cause the sleeve to contact the sides of the wound and expand the wound for surgery. The sides of the wound are also protected by the sleeve from contamination during surgery. These wound edge protectors are typically not adjustable and numerous different sized retractors are required having varying sized rings and/or sleeve lengths for different sized wounds.

In another known wound edge protector, the circumference of the wound edge protector is adjustable by use of telescoping inner and outer rings and overlapping lengthwise sleeve edges.

Also known is an incision liner and retractor which is similar in construction to wound edge protectors. In the incision liner and retractor, the length of the sleeve is incrementally adjustable by rolling the sleeve onto the circumference of the outer ring by rotating the outer ring about its central axis. In one example, the outer ring has an oblate cross-section with opposed flat chordal surfaces to assist in rotating the ring about its central axis. However, manually rotating the outer ring about its central axis is often difficult. An example of such an incision liner and retractor is found in U.S. Pat. No. 5,524,644.

SUMMARY OF THE INVENTION

In one aspect of the invention, an adjustable retractor is disclosed. The adjustable retractor comprises an inner ring, an outer ring spaced from the inner ring, and an elongate sleeve open at opposite ends. The sleeve extends between the inner and outer rings and is connected at its opposite ends to the inner and outer rings. The outer ring is provided with a pre-loaded rotational torque to assist with rotation of the outer ring about its central axis to roll the sleeve about the outer ring to adjust sleeve length.

According to one embodiment, the outer ring is formed in a mobius configuration to provide the pre-loaded rational torque of the outer ring. In the mobius configuration, an outer circumference is rotationally offset or twisted by a predetermined amount about the central axis of the outer ring along the length of the ring. The outer ring may include a tube having two ends secured together, the circumferences of the ends being offset from one another. The offset may be gradual, proceeding longitudinally along the central axis of the outer ring. In another embodiment, the offset may be discontinuous or occur in at least one step. According to another embodiment, the circumference is offset at least about 20° about the central axis of the outer ring. The circumference may be offset between about 45° and about 540° about the central axis of the outer ring. In another embodiment, the predetermined amount of the offset may be about 180° or about 360°.

In another embodiment, the cross-section may be shaped in numerous different configurations including substantially circular, substantially triangular, substantially star-shaped having at least four points, substantially parallelogram, substantially polygonal, or substantially cruciform.

According to another embodiment, the one location has a cross-sectional shape that matches a cross-sectional shape at the other location. The outer circumference of the outer ring at the one location may be offset with respect to the outer circumference at the other location about the central axis of the outer ring by an amount to match the cross-sectional shape at the one location with the cross-sectional shape at the other location. The outer circumference of the cross-section at the one location may be offset 180° about the central axis of the outer ring to with respect to the outer circumference at the other location.

According to another embodiment of the invention, in operation the entire outer ring is rotatable manually about its central axis. The sleeve may be a thin, flexible sheet having overlapping sealed edges to form a cylinder. In yet another embodiment, the sleeve may be seamless. The opposite ends of the sleeve may be wrapped about the rings and secured to the sleeve. The inner ring may be squeezable into an oblong shape for insertion into a surgical incision and may be constructed to return to its original shape when released to bear against an inner edge of a surgical incision. Length of the sleeve may be adjustable to locate the outer ring against an outer edge of a surgical incision. The length of the sleeve may be adjustable before or after insertion of the inner ring into a surgical incision.

In another embodiment of this aspect of the invention, an adjustable retractor comprises an inner ring squeezable into an oblong shape for insertion into a surgical incision and structured to return to its original shape to bear against an inner edge of the surgical incision. An outer ring is spaced from the inner ring, the outer ring being formed in a mobius configuration. A sleeve having two ends extends between the inner and outer rings. The inner and outer rings are secured to the opposite ends of the sleeve. The outer ring in operation is rotatable about its central axis to roll the sleeve about itself and the outer ring and thereby adjust sleeve length to locate the outer ring adjacent an outer edge of the surgical incision.

In one embodiment, the outer ring has a cross-sectional shape, the mobius configuration may include one location on an outer circumference of the outer ring rotationally offset with respect to another location by a predetermined amount about the central axis of the outer ring. The offset may be gradual, proceeding longitudinally along the central axis of the outer ring. In another embodiment, the offset may be discontinuous or occur in at least one step. The outer circumference may be offset at least about 20° about the central axis of the outer ring. In another embodiment, the outer circumference may be offset between about 45° and about 540° about the central axis of the outer ring. The one location may have a cross-sectional shape that matches a cross-sectional shape at the other location. The outer circumference of the outer ring at the one location may be offset with respect to the outer circumference at the other location about the central axis of the outer ring by an amount to match the cross-sectional shape at the one location with the cross-sectional shape at the other location. The outer circumference of the cross-section at the one location may be offset 180° about the central axis of the outer ring to with respect to the outer circumference at the other location. The outer ring may have a cross-sectional shape in numerous different configurations.

In yet another aspect of the invention, a method of adjusting a retractor is disclosed. The method comprises the steps of: providing an inner and an outer ring spaced apart from one another, providing an elongate sleeve extending between the inner and outer rings, the sleeve having a length and two opposed ends, each end being secured to one of the inner and outer rings, providing a pre-loaded rotational torque on the outer ring, and adjusting the length of the sleeve by rotating the outer ring about its central axis with the assistance of the pre-loaded torque to roll the sleeve about itself and the outer ring to adjust sleeve length. According to one embodiment, the outer ring is formed in a mobius configuration to provide the pre-loaded rotational torque on the outer ring.

BRIEF DESCRIPTION OF THE DRAWINGS

The objects, advantages and features of this invention will be more clearly appreciated from the following detailed description, when taken in conjunction with the accompanying drawings, wherein like numbers are used for like features, in which.

DETAILED DESCRIPTION

Figure 1:
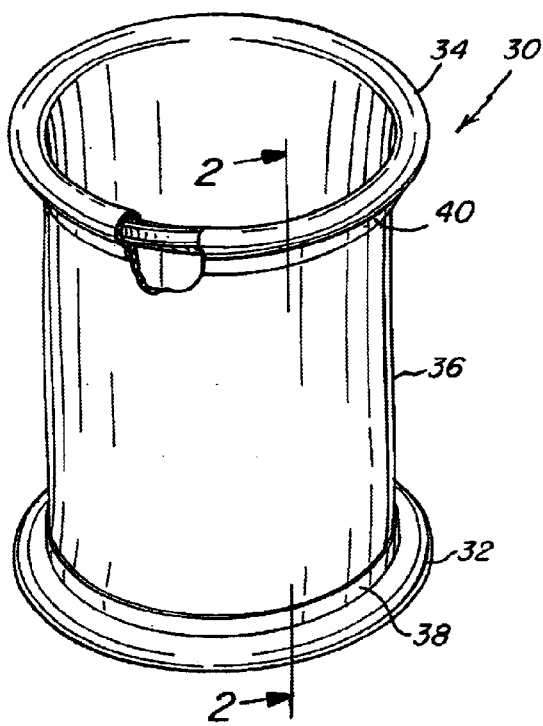
FIG. 1 is a partially broken-away perspective view of one embodiment of a retractor according to the present invention, in a fully extended state.
Figure 2:
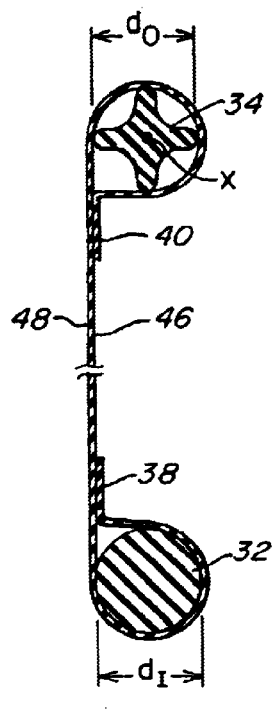
FIG. 2 is a cross-sectional view of the retractor of FIG. 1 taken along line 2—2 of FIG. 1.

With reference now to the drawings, and more particularly to FIGS. 1 and 2 thereof, one aspect of this invention features a retractor 30. Retractor 30 includes an inner ring 32 and an outer ring 34 spaced from inner ring 32. An elongate sleeve 36 having two opposed ends 38 and 40 is provided and extends between inner and outer rings 32 and 34. One opposed end 38 is secured to inner ring 32 and the other end 40 is secured to outer ring 34.

In one embodiment of the invention, sleeve 36 is a flexible tubular sheet having a substantially uniform circumference between ends 38 and 40. Preferably, the sleeve is nonflammable, physiologically inert, substantially impermeable to fluid and bacteria, and resistant to melting. In one embodiment, sleeve 36 is made of a polyurethane thin film, although other suitable materials may be used, such as polyolefins. The sleeve material may be substantially transparent and may have any desired color. Sleeve 36 may be produced in any suitable manner, for example in a seamless tubular form, or by a flat sheet which is formed into a tubular shape and in which the longitudinal edges of the sleeve are overlapped and sealed to one another. Sleeve 36 may have any desired length L when secured to inner and outer rings 32 and 34; however, its length will depend on the type of surgeries to be performed with retractor 30. It is preferable that the sleeve length L be long enough to accommodate incisions having walls of different thickness $I_{WT}$. Diameter $D_S$ of sleeve 36 will also vary depending on the size of the incision used in the surgeries to be performed with retractor 30.

As shown in FIGS. 2 and 5–7, inner ring 32 typically has a substantially round cross-sectional shape. It will be appreciated, however, that the cross-sectional shape of the inner ring may be any desired configuration. Furthermore, the cross-sectional shapes of inner and outer rings 32 and 34 may be the same or different. The cross-sectional shape of inner ring 32 has a particular diameter $d_I$. Diameter $d_I$ may be any suitable length; however, the length selected will depend on a number of factors, including at least overall diameter $D_I$ of inner ring 32, the material selected, and the cross-sectional shape of inner ring 32. Inner ring 32 is preferably capable of being squeezed into a substantially oblong shape for insertion into an incision, and is capable of returning back to its original shape, for example after insertion into the body. As shown, inner ring 32 has a substantially circular shape. However, it will be appreciated that inner ring 32 may have any other suitable shape, for example oval. Inner ring 32 may be formed in any suitable manner. For example, inner ring 32 may be molded as one-piece or inner ring 32 may be formed of a length of tube having two ends, with the ends being secured together.

As shown in FIGS. 1 and 2, opposed ends 38 and 40 of sleeve 36 are secured to inner and outer rings 32 and 34, respectively. As shown in FIG. 2, opposed ends 38 and 40 of sleeve 36 are preferably wrapped about respective rings 32 and 34 at least once and are then secured, such as by heat sealing sleeve 36 to itself. Preferably, opposed ends 38 and 40 are secured to outside surface 46 of sleeve 36. It will be appreciated that sleeve 36 may be secured in any other suitable manner to inner and outer rings 32 and 34. For example, opposed ends 38 and 40 may be wrapped around the rings 32 and 34 and secured to inside surface 48 of sleeve 36.

Figure 3:
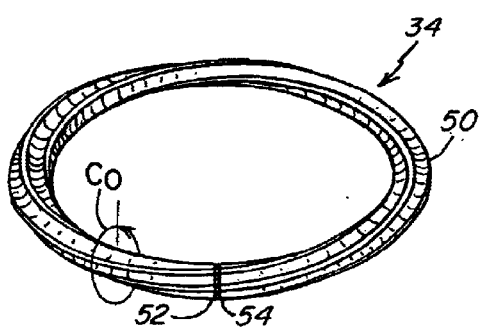
FIG. 3 is a perspective view of one embodiment of an outer ring according to the invention.
Figure 4:
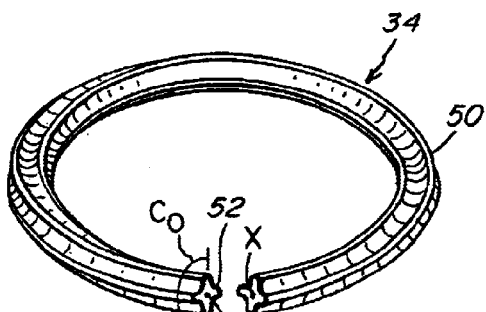
FIG. 4 is a perspective view of another embodiment of an outer ring according to the invention.

Referring now to FIGS. 2–4, outer ring 34 has a size which is substantially similar to that of inner ring 32. Outer ring 34 may have almost any desired cross-sectional shape, as described in further detail below. Outer ring 34 has a central axis X as shown in FIG. 2 that extends through the cross-sectional center of outer ring 34 along its entire length. The cross-sectional shape has a largest diameter $d_O$, and may be any desired length. However, the length selected will depend on a number of factors, including at least overall diameter $D_O$ of outer ring 34, the material selected, and the cross-sectional shape of outer ring 34. Outer ring 34 is configured so that outer circumference C thereof may be rotated about its central axis X. As shown in FIGS. 1, 3 and 4, outer ring 34 has a substantially circular shape. However, it will be appreciated that outer ring 34 may have any other suitable shape, for example oval.

Outer ring 34 has a pre-loaded rotational torque to assist with or facilitate rotation of the outer ring about its central axis X. In one preferred embodiment, the outer ring 34 is formed in a mobius configuration to provide the pre-loaded rotational torque. As used herein, the term mobius configuration includes any configuration in which outer circumference C of the cross-section of outer ring 34 is offset, twisted or rotated by a predetermined amount $C_O$ about the central axis X of outer ring 34 proceeding longitudinally or lengthwise along the central axis X of outer ring 34 from one location 52 on outer ring 34 to another location 54. Locations 52 and 54 typically abut one another or are adjacent one another. The rotation or offset may be gradual, discontinuous, or it may occur in discrete steps or it may occur only at locations 52 and 54. For example as shown in FIGS. 3 and 4, outer circumference C of tube 50 is twisted or rotated about central axis X by a certain amount such that the locations 52 and 54 of the tube 50 are rotationally offset from one another by an amount $C_O$, and the offset changes gradually and continuously from zero at location 52 to $C_O$ at location 54.

In one example, locations 52 and 54 are defined by two ends of a straight tube that are joined together to form outer ring 34, and the rotational offset $C_O$ is observed where the ends are joined together. This rotational offset about central axis X increases gradually and uniformly moving along central axis X along the length of outer ring 34 from location 52 to location 54. Locations or ends 52 and 54 of tube 50 may be bonded together by any suitable method. Tube 50 may be extruded, cut to the desired length, twisted and then ends 52 and 54 may be bonded together to form outer ring 34. Of course, it will be understood that outer ring 34 may be formed in any other suitable manner, such as by being molded as a single-piece or as multiple pieces and still include the mobius configuration.

The total rotational offset $C_O$ may be any desired amount. Preferably, the total offset $C_O$ is at least about 20°. More preferably, the total offset $C_O$ is between about 45° and about 540° about the central axis X of outer ring 34. As shown in FIG. 3, the total offset $C_O$ is 360°, so that outer ring 34 is twisted an equivalent of a full turn about its central axis X. As shown in FIG. 4, the total offset $C_O$ is 180°, so that tube 50 is twisted an equivalent of one-half turn about central axis X such that where the cross-sections at locations 52 and 54 mate with one another, they are offset by one-half turn.

This mobius configuration of outer ring 34 pre-loads outer ring 34 with rotational torque, such that the offset $C_O$ facilitates rotation of outer ring 34 about its central axis X. Outer ring 34 may be turned either outwardly or inwardly, but once outer ring 34 is partially rotated about its central axis X the remainder of outer ring 34 will tend to rotate on its own to complete the twisting motion because of the pre-loaded rotational torque.

Outer ring 34 may have any desired cross-sectional shape. Particular cross-sectional shapes will be discussed below for exemplary purposes only. In one example, as shown in the embodiment of FIGS. 1–7, outer ring 34 has a substantially cruciform cross-sectional shape. Generally, the cruciform cross-sectional shape includes a circle from which four regularly spaced circular arcs of a somewhat larger radius have been excised, resulting in a cross-sectional shape formed of eight circular segments that are alternately concave and convex.

Figure 8:
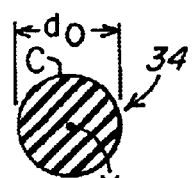
FIG. 8 is a cross-sectional view of another embodiment of the outer ring according to the invention.

In another example, as shown in FIG. 8, outer ring 34 may have a substantially circular cross-sectional shape. The circumference of FIG. 8 may be offset by any desired amount $C_O$ about the central axis X of the outer ring 34. However, it will be understood that a greater amount of offset will make the outer ring easier to rotate about its central axis X by providing more pre-loaded torque, while too much offset will also not be optimal.

Figure 9:
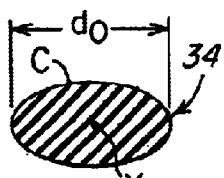
FIG. 9 is a cross-sectional view of yet another embodiment of the outer ring according to the invention.
Figure 10:
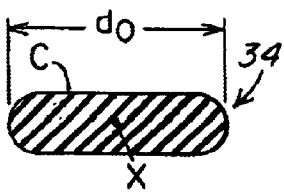
FIG. 10 is a cross-sectional view of yet another embodiment of the outer ring according to the invention.
Figure 11:
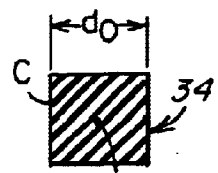
FIG. 11 is a cross-sectional view of yet another embodiment of the outer ring according to the invention.
Figure 12:
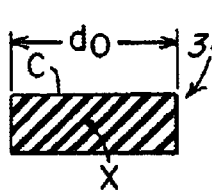
FIG. 12 is a cross-sectional view of yet another embodiment of the outer ring according to the invention.

Referring now to FIGS. 9 and 10, other exemplary cross-sectional shapes for outer tube 34 are illustrated. FIG. 9 shows an elliptical cross-sectional shape, while FIG. 10 shows an oblate cross-sectional shape having flat chordal surfaces opposite one another. Either of these cross-sectional shapes may be offset or rotated in multiples of 180° about the central axis X of outer ring 34 so that matching portions of the circumference are matched with one another. However, it will be appreciated that the circumference may be offset by any desired amount $C_O$, as the matching portions thereof do not need to mate with one another.

Figure 13:
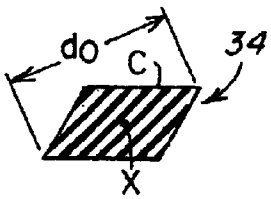
FIG. 13 is a cross-sectional view of yet another embodiment of the outer ring according to the invention.
Figure 14:
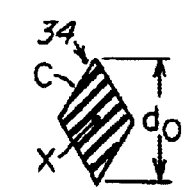
FIG. 14 is a cross-sectional view of yet another embodiment of the outer ring according to the invention.
Figure 15:
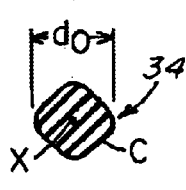
FIG. 15 is a cross-sectional view of yet another embodiment of the outer ring according to the invention.

FIGS. 11–15 show various parallelogram cross-sectional shapes that could be used for outer ring 34. These parallelogram cross-sectional shapes include a square (FIG. 11), a rectangle (FIG. 12) and a diamond (FIGS. 13 and 14). Each has a largest cross-sectional dimension, $d_O$. It will be appreciated that corners of the cross-sectional shapes may be rounded or pointed. It will also be appreciated that the circumferences may be offset by any desired amount $C_O$ about the central axis X of the outer ring 34. For example, the circumference of FIG. 11 may be rotationally offset a quarter turn (90°), a half-turn (180°), a three-quarter turn (270°), a full turn (360°) or multiples of thereof, such that the circumferences of locations 52 and 54 mate with one another on outer ring 34 in a seamless manner. However, it will be appreciated that the circumference may be offset about the central axis X of outer ring 34 by an amount that does not align the cross-sectional shapes of locations 52 and 54 in a seamless manner.

Figure 16:
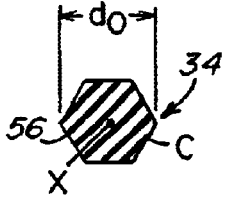
FIG. 16 is a cross-sectional view of yet another embodiment of the outer ring according to the invention.

FIG. 16 shows a polygonal cross-sectional shape having six sides or a hexagonal cross-sectional shape. It will be understood that a polygonal cross-sectional shape may have any number of sides 56. Once again, the circumference may be rotationally offset by a desired amount about the central axis X of outer ring 34, such that matching portions of the cross-sectional shape mate with one another at locations 52 and 54 or such that they do not mate with one another at locations 52 and 54. In order to determine the amount to offset the circumference to mate matching cross-sectional portions at locations 52 and 54, the circumference may be offset by 360° divided by the number of sides 56 of the polygon, or multiples thereof.

Figure 17:
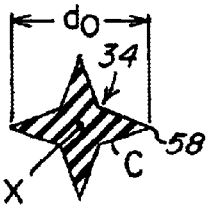
FIG. 17 is a cross-sectional view of yet another embodiment of the outer ring according to the invention.
Figure 18:
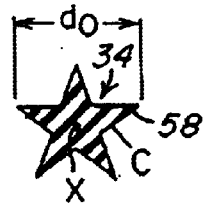
FIG. 18 is a cross-sectional view of yet another embodiment of the outer ring according to the invention.
Figure 19:
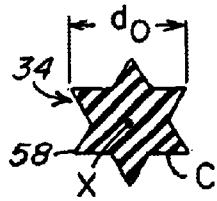
FIG. 19 is a cross-sectional view of yet another embodiment of the outer ring according to the invention.
Figure 20:
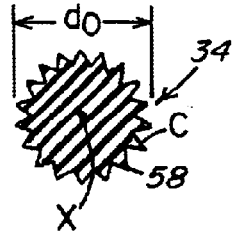
FIG. 20 is a cross sectional view of yet another embodiment of the outer ring according to the invention.

FIGS. 17–20, show star cross-sectional shapes for outer ring 34. It will be understood that a star cross-sectional shape having any number of points 58 may be used. For the purposes of illustration only, FIG. 17 shows a star with four points 58, FIG. 18 shows a star with five points 58, FIG. 19 shows a star with six points 58, and FIG. 20 shows a star with 18 points 58. Moreover, it will be understood that the circumference may be rotationally offset about the central axis X of outer ring 34, by the number of points 58 divided by 360° or multiples thereof to mate matching points 58 of the star at locations 52 and 54. For example, the four point star may be offset by 90°, 180°, 270° and 360° or multiples thereof, while the eighteen point star may be offset by any increment of 20° (360° divided by the 18 points of the star). Of course, as before it will be appreciated that it is not necessary to mate matching points 58 of the stars with one another when the circumference is offset about the central axis X of outer ring 34.

Figure 21:
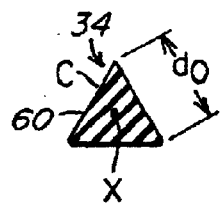
FIG. 21 is a cross-sectional view of yet another embodiment of the outer ring according to the invention.

FIG. 21 shows a triangular cross-sectional shape for outer ring 34. The triangular cross-sectional shape may have sides 60 of equal or unequal length. In one embodiment, for an equilateral triangle, the circumference may be offset about the central axis X of outer ring 34 by 120°, 240° and 360°, or multiples thereof to mate matching sides of the triangular cross-sectional shape with one another at locations 52 and 54. Of course, it will be appreciated that the circumference may be offset by an amount that does not mate the sides of the triangular cross-sectional shapes with one another at locations 52 and 54.

Figure 22:
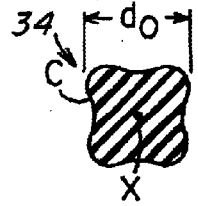
FIG. 22 is a cross-sectional view of yet another embodiment of the outer ring according to the invention.
Figure 23:
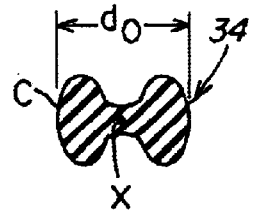
FIG. 23 is a cross-sectional view of yet another embodiment of the outer ring according to the invention.

FIG. 22 shows another embodiment of the cruciform cross-sectional shape of FIGS. 1–7. FIG. 23 shows a dog-bone cross-sectional shape. It will be appreciated that the circumference of these figures may be offset by any desired amount $C_O$ at locations 52 and 54, as described above. It will also be understood that any of the cross-sectional shapes described above or other possible cross-sectional shapes may be irregular, such as a rhombus shaped cross-section. It will also be understood that the examples of cross-sectional shapes illustrated above are not intended to limit the invention disclosed herein and that many other possible shapes for outer ring 34 may be used in accordance with this invention.

Inner and outer rings 32 and 34 are preferably made of a medical grade polyurethane material. In one embodiment, the material of inner and outer rings 32 and 34 has between about 70 and about 90 durometer, Shore A. It will be understood that any other suitable material could be used, such as polyethylene or polypropylene. The material of inner and outer rings 32 and 34 may be the same or different. The material of inner ring 32 will preferably allow inner ring 32 to be squeezed into an oblong shape for insertion into the incision and still return to its original shape when inner ring 32 is in place against an inner edge 42 of the incision. The material of outer ring 34 will preferably allow the circumference of outer ring 34 to be rotated about its central axis X using a thumb and fingers and still allow outer ring 34 to be stable when located against an outer edge 44 of the incision.

Inner and outer rings 32 and 34 have respective diameters $D_I$ and $D_O$ that may vary depending on the size of the incision to be used with retractor 30. Generally, the greater the diameter of the rings, the greater is the durometer of the preferred material, while the smaller the diameter, the lower is the durometer of the preferred material. Of course, it will be appreciated that the durometer of the material would change less for small incremental changes in diameter of rings 32 and 34 (i.e. on the order of 20 mm). Also, diameters $D_I$ and $D_O$ of inner and outer rings 32 and 34 and diameter $D_S$ of sleeve 36 are preferably substantially similar, although they could be different from one another. Inner and outer rings 32 and 34 may be different colors. For example, inner ring 32 may be red, while outer ring 34 may be substantially transparent.

Figures 5, 6, 7:
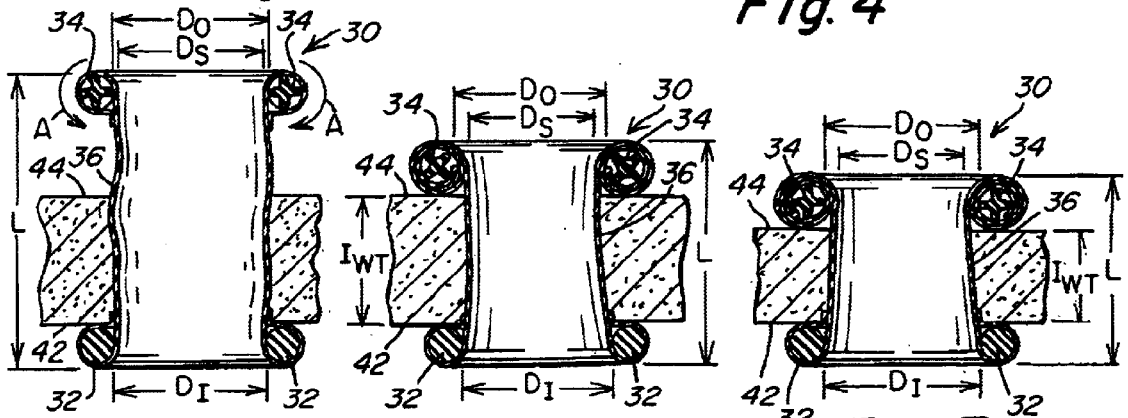
FIG. 5 is a cross-sectional schematic view of the retractor of FIG. 1 partially installed in a surgical incision.
FIG. 6 is a cross-sectional schematic view of the retractor of FIG. 5 completely installed in the surgical incision.
FIG. 7 is a cross-sectional schematic view of the retractor of FIG. 1 completely installed in a surgical incision having a thinner wall than the incision of FIGS. 5 and 6.

The mobius configuration of outer ring 34 described above facilitates the rolling and unrolling of sleeve 36 onto outer ring 34 to adjust sleeve length L. One illustrative method of adjusting sleeve length L according to the invention, will now be discussed. To shorten the length L of sleeve 36, a thumb and forefinger of each hand may be placed on outer ring 34 of retractor 30. For example, the left hand may be placed at about the 10 o'clock position and the right hand may be placed at about the 2 o'clock position on outer ring 34. The outer surface of outer ring 34 is grasped by each hand and outer ring 34 is rotated or turned outwardly about central axis X away from sleeve 36 in the same (i.e. at the 10 and 2 o'clock) direction, as shown in FIG. 5 by the direction of arrows A. Once part of outer ring 34 about central axis X is rotated outwardly the remainder of outer ring 34 will continue to rotate outwardly about central axis X until all of outer ring 34 has been rotated a full turn (i.e. about 360°) about its central axis X, because of the pre-loaded torque caused by the mobius configuration. As outer ring 34 is rotated outwardly about its central axis X, the sleeve 36 is rolled onto outer ring 34 thereby shortening its length L. Thus, retractor 30 may be used on incisions having a different wall thickness $I_{WT}$ as shown in FIGS. 6 and 7. The incision of FIG. 6 has a greater wall thickness $I_{WT}$ than that of FIG. 7, yet the same retractor 30 may be used to expand both incisions for surgery. Sleeve 36 in either case may be drawn tight against the wall to expand the incision for surgery.

Sleeve 36 may be lengthened in much the same manner after being shortened by rotating or turning outer ring 34 in the opposite direction or inwardly. Once again, as part of outer ring 34 is rotated inwardly, the remainder of outer ring 34 will continue to rotate inwardly until outer ring 34 has been rotated a full turn (i.e. about 360°) about its central axis X. As outer ring 34 is rotated inwardly about its central axis X, sleeve 36 is unrolled from outer ring 34, thereby lengthening the sleeve length L.

It will be appreciated that one or two hands may be used to rotate or turn outer ring 34 outwardly or inwardly thereby using the pre-loaded torque of outer ring 34 resulting from the mobius configuration to facilitate the rotation of outer ring 34. It will also be understood that outer ring 34 could be rotated inwardly to shorten sleeve 36 and rotated outwardly to lengthen sleeve 36. Moreover, it will be appreciated that a separate device may be used to assist in rotating outer ring 34 outwardly or inwardly to roll or unroll sleeve 36 on outer ring 34. For example, a device could be provided on the outer circumference of outer ring 34 to follow one of its surfaces, in either a clockwise or counter-clockwise direction, and cause the surface to always be located on the outside circumference thereby rotating the ring outwardly or inwardly about its central axis to shorten or lengthen the sleeve length.

As described in U.S. Pat. No. 5,524,644, retractor 30 of the present invention may be used during surgery. In one example, retractor 30 may be used in a minimally invasive abdominal surgical procedure. The abdomen is routinely prepared with antiseptic and dried; the site for the incision is traced on the abdomen and covered with a surgical drape; and a muscle split or incision is made at the site through the peritoneum. Retractor 30 is placed though the incision by squeezing inner ring 32 into an oblong shape and inserting it lengthwise through the incision and letting it return to its original shape inside the peritoneum around the inner edge 42 of the incision. Outer ring 34 may be gripped by the thumb and forefinger of both hands and rotated outwardly (as shown in FIG. 5 and discussed above), rolling sleeve 36 onto outer ring 34 until outer ring 34 abuts the outer edge 44 of the incision, as shown in FIGS. 6 and 7. The part of sleeve 36 in the incision between inner and outer rings 32 and 34 is thereby drawn into contiguous contact with the sides of the incision to expand the incision for surgery and provide a self-retaining, protective barrier for surgery. If desired, retractor 30 may be pre-adjusted prior to insertion, or partially pre-adjusted prior to surgery. The mobius configuration of outer ring 34 facilitates rotation of outer ring 34 about its central axis X to shorten or lengthen sleeve 36 by rolling or unrolling the sleeve on or off the outer ring. The mobius configuration also assists in keeping outer ring 34 from unrolling during surgery after the outer ring is in place adjacent the outer edge 44 of the incision.

Modifications and improvements within the scope of this invention will occur to those skilled in the art. The above description is intended to be exemplary only. The scope of this invention is defined only by the following claims and their equivalents.

What is claimed is:

1. An adjustable retractor, comprising:
   an inner ring;
   an outer ring spaced from the inner ring; and
   an elongate sleeve open at opposite ends, the sleeve extending between the inner and outer rings and being connected at opposite ends to the rings,
   wherein the outer ring is provided with a pre-loaded rotational torque to assist with rotation of the outer ring about its central axis to roll the sleeve about the outer ring to adjust sleeve length.

2. The retractor of claim 1, wherein the outer ring is formed in a mobius configuration to provide the pre-loaded rotational torque, the mobius configuration including one location on an outer circumference of the outer ring rotationally offset with respect to another location by a predetermined amount about the central axis of the outer ring.

3. The retractor of claim 2 wherein the outer ring includes two ends secured together, the outer circumference of one end being rotationally offset with respect to the outer circumference of the other end.

4. The retractor of claim 2 wherein the offset is gradual, proceeding longitudinally along the central axis of the outer ring.

5. The retractor of claim 2 wherein the offset is discontinuous.

6. The retractor of claim 2 wherein the offset occurs in at least one step.

7. The retractor of claim 2 wherein the outer circumference of the outer ring is offset at least about 20° about the central axis of the outer ring.

8. The retractor of claim 2 wherein the outer circumference of the outer ring is offset between about 45° and about 540° about the central axis of the outer ring.

9. The retractor of claim 2 wherein the predetermined amount is about 180°.

10. The retractor of claim 2 wherein the predetermined amount is about 360°.

11. The retractor of claim 2 wherein the outer ring has a substantially circular cross-sectional shape.

12. The retractor of claim 2 wherein the outer ring has a substantially triangular cross-sectional shape.

13. The retractor of claim 2 wherein the outer ring has a substantially star-shaped cross-sectional shape having at least four points.

14. The retractor of claim 2 wherein the outer ring has a substantially parallelogram cross-sectional shape.

15. The retractor of claim 2 wherein the outer ring has a substantially polygonal cross-sectional shape.

16. The retractor of claim 2 wherein the outer ring has a substantially cruciform cross-sectional shape.

17. The retractor of claim 2 wherein the one location has a cross-sectional shape that matches a cross-sectional shape at the other location and wherein the outer circumference of the outer ring at the one location is offset with respect to the outer circumference at the other location about the central axis of the outer ring by an amount to match the cross-sectional shape at the one location with the cross-sectional shape at the other location.

18. The retractor of claim 17 wherein the outer circumference of the cross-section at the one location is offset 180° about the central axis of the outer ring to with respect to the outer circumference at the other location.

19. The retractor of claim 1 wherein in operation the entire outer ring is manually rotatable about its central axis.

20. The retractor of claim 1 wherein the sleeve is a thin, flexible sheet having overlapping sealed edges to form a cylinder.

21. The retractor of claim 1 wherein the sleeve is seamless.

22. The retractor of claim 1 wherein the opposite ends of the sleeve are wrapped about the rings and secured to the sleeve.

23. The retractor of claim 1 wherein the inner ring is squeezable into an oblong shape for insertion into a surgical incision and constructed to return to its original shape when released to bear against an inner edge of a surgical incision.

24. The retractor of claim 23 wherein length of the sleeve is adjustable to locate the outer ring against an outer edge of a surgical incision.

25. The retractor of claim 24 wherein the length of the sleeve is adjustable before or after insertion of the inner ring into a surgical incision.

26. An adjustable retractor, comprising:
   an inner ring squeezable into an oblong shape for insertion into a surgical incision and structured to return to its original shape to bear against an inner edge of the surgical incision;
   an outer ring spaced from the inner ring, the outer ring being formed in a mobius configuration; and
   a sleeve having two ends the sleeve extending between the inner and outer rings, the inner and outer rings being secured to opposite ends of the sleeve,
   wherein the outer ring in operation is rotatable about its central axis to roll the sleeve about itself and the outer ring and thereby adjust sleeve length to locate the outer ring adjacent an outer edge of the surgical incision.

27. The retractor of claim 26 wherein the outer ring has a cross-sectional shape, the mobius configuration including one location on an outer circumference of the outer ring rotationally offset with respect to another location by a predetermined amount about the central axis of the outer ring.

28. The retractor of claim 27 wherein the offset is gradual, proceeding longitudinally along the central axis of the outer ring.

29. The retractor of claim 27 wherein the offset is discontinuous.

30. The retractor of claim 27 wherein the offset occurs in at least one step.

31. The retractor of claim 27 wherein the outer circumference of the outer ring is offset at least about 20° about the central axis of the outer ring.

32. The retractor of claim 27 wherein the outer circumference of the outer ring is offset between about 45° and about 540° about the central axis of the outer ring.

33. The retractor of claim 27 wherein the one location has a cross-sectional shape that matches a cross-sectional shape at the other location and wherein the outer circumference of the outer ring at the one location is offset with respect to the outer circumference at the other location about the central axis of the outer ring by an amount to match the cross-sectional shape at the one location with the cross-sectional shape at the other location.

34. The retractor of claim 33 wherein the outer circumference of the cross-section at the one location is offset 180° about the central axis of the outer ring to with respect to the outer circumference at the other location.

35. The retractor of claim 26 wherein the outer ring has a substantially circular cross-sectional shape.

36. The retractor of claim 26 wherein the outer ring has a substantially triangular cross-sectional shape.

37. The retractor of claim 26 wherein the outer ring has a substantially star cross-sectional shape having at least four points.

38. The retractor of claim 26 wherein the outer ring has a substantially parallelogram cross-sectional shape.

39. The retractor of claim 26 wherein the outer ring has a substantially polygonal cross-sectional shape.

40. The retractor of claim 26 wherein the outer tube has a substantially cruciform cross-sectional shape.

41. A method of adjusting a retractor, the method comprising the steps of:
    providing an inner and an outer ring spaced apart from one another;
    providing an elongate sleeve extending between the inner and outer rings, the sleeve having a length and two opposed ends, each end being secured to one of the inner and outer rings;
    providing a pre-loaded rotational torque on the outer ring; and
    adjusting the length of the sleeve by rotating the outer ring about its central axis with the assistance of the pre-loaded torque to roll the sleeve about itself and the outer ring to adjust sleeve length.

42. The method of claim 41, wherein the outer ring is formed in a mobius configuration to provide the pre-loaded rotational torque on the outer ring.

* * * * *

UNITED STATES PATENT AND TRADEMARK OFFICE
CERTIFICATE OF CORRECTION

PATENT NO.     : 6,723,044 B2
DATED          : April 20, 2004
INVENTOR(S)    : John C. Pulford and Marco Pelosi It is certified that error appears in the above-identified patent and that said Letters Patent is hereby corrected as shown below:

Column 10,
Line 30, after "outer ring", please delete the word "to"

Column 11,
Line 28, after "outer ring", please delete the word "to"

Signed and Sealed this

Seventeenth Day of August, 2004

JON W. DUDAS
*Acting Director of the United States Patent and Trademark Office*